United States Patent [19]

Fedorov et al.

[11] Patent Number: 5,042,490

[45] Date of Patent: Aug. 27, 1991

[54] METHOD FOR DIAGNOSIS OF EARLY STAGE OF OPTIC NERVE BLOOD SUPPLY DISTURBANCE

[76] Inventors: Svyatoslav N. Fedorov, Pereulok Dostoveskogo, 1/21, kv. 32, Moscow, U.S.S.R.; Merrill P. Spencer, 5129 NE. Laurel Crest La., Seattle, Wash. 98105; Gertruda D. Mikhailova, Ulitsa Dubninskaya, 63, korpus 3, kv. 18; Dina I. Ioffe, Ukrainsky Bulvar, 3/5, korpus 2, kv. 33, both of Moscow, U.S.S.R.

[21] Appl. No.: 405,549

[22] Filed: Sep. 11, 1989

[30] Foreign Application Priority Data

Sep. 14, 1988 [SU] U.S.S.R. ............................... 4483593

[51] Int. Cl.$^5$ ................................................ A61B 8/06
[52] U.S. Cl. ............................ 128/661.09; 128/661.06
[58] Field of Search ..................... 128/661.07–661.10, 128/661.06, 662.03–662.04, 745

[56] References Cited

U.S. PATENT DOCUMENTS 4,907,595  3/1990  Strauss ........................... 128/661.07

Primary Examiner—Francis Jaworski
Attorney, Agent, or Firm—Burgess, Ryan & Wayne

[57] ABSTRACT

The invention is a method for diagnosis of early stage of optic nerve blood supply disturbance resides in that the state and localization of the optic nerve is determined by virtue of ultrasonic scanning, then a distance from the eyelid anterior surface of the ciliary arteries supplying said optic nerve is measured, whereupon the state of hemodynamics in said ciliary arteries is determined on the thus-measured distance with the aid of ultrasonic pulse-dopplerography, by measuring the linear and volumetric blood flow velocities in said arteries, a value of said linear blood flow velocity below 9 cm/s and of said volumetric blood flow below 5 ml/min are indicative of an early stage of optic nerve blood supply disturbance.

1 Claim, No Drawings

METHOD FOR DIAGNOSIS OF EARLY STAGE OF OPTIC NERVE BLOOD SUPPLY DISTURBANCE

FIELD OF THE INVENTION

This invention relates generally to medicine and more specifically to a method for diagnosis of an early stage of optic nerve blood supply disturbance, which is applicable in ophthalmological practice and is aimed at prevention of optic nerve atrophy in persons with a reduced blood supply of the optic nerve, as well as at timely treatment of still developing optic nerve atrophy, using surgical, therepeutic, or physical methods.

BACKGROUND OF THE INVENTION

Known in the present state of the art are methods for studying the state of the eyeball blood supply, e.g., a method involving the recording of the parameters of the eyeball hemodynamics, the linear velocity of the blood flow in the ophthalmic artery in the area of two-thirds of the superciliary arch (SU, A, 1,120,998).

The aforementioned method cannot, however, be employed for diagnosis of an early stage of optic nerve blood supply disturbance, since it fails to determine the state of the optic nerve hemodynamics.

One more state-of-the-art method for studying the state of the eyeball blood supply is known to consist in that there is carried out successively compression of the superficial temporal artery, the angular artery and the maxillary artery and simultaneously there is recorded successively the linear velocity of the blood flow in the ophthalmic artery, while the state of the eyeball blood supply at a given instant is determined according to that artery or a combination of arteries, the compression of which results in the maximum blood flow velocity along the ophthalmic artery (SU, A, 1,388,030).

The method mentioned above, however, fails to determine the state of the optic nerve hemodynamic parameters, such as volumetric and linear blood flow velocity in the ciliary arteries supplying the optic nerve; therefore, the method cannot be used for diagnosis of an early state of optic nerve blood supply disturbance.

SUMMARY OF THE INVENTION

It is an object of the present invention to provide a method for diagnosis of an early stage of optic nerve blood supply disturbance.

Said object is accomplished by a method for diagnosis of an early stage of optic nerve blood supply disturbance according to the invention, the state and localization of the optic nerve is determined by virtue of ultrasonic scanning, then a distance from the eyelid anterior surface to the ciliary arteries supplying said optic nerve is measured, whereupon the state of hemodynamics in said ciliary arteries is determined on the thus-measured distance, with the aid of ultrasonic pulse-dopplerography, by measuring the volumetric blood flow an linear blood flow velocities in said arteries, so that the value of said linear blood flow velocity if below 9 cm/s and that of said volumetric blood flow if below 5 ml/min are indicative of an early stage of optic nerve blood supply disturbance.

Practical application of the herein-proposed method makes it possible to improve occupational rehabilitation of patients suffering from, or suspected of optic nerve atrophy by timely treatment of optic nerve blood supply insufficiency.

Detailed Description of the Invention

The state of the optic nerve hemodynamics is examined through the closed eyelids in order to avoid any influence of anesthetic drops upon the reliability of the findings thus obtained. Examination of a control group of volunteers free from any eye diseases revealed that the linear blood flow velocity in the ciliary arteries supplying the optic nerve, equals 9 cm/s and an average volumetric blood flow therein is equal to 5 ml/min.

The method of the invention is carried into effect as follows.

The patient is examined in a sitting posture with the eyes closed. Then a sagittal eye tomogram at the level of the optic nerve is obtained by virtue of ultrasonic scanning and is presented on a display. Next a distance from the eyelid anterior surface to the projection of the ciliary arteries supplying the optic nerve, is measured on the eye scanogram thus obtained. The data obtained (i.e., the measured distance) are entered into a pulsating wave ultrasonic Doppler instrument (pulse-Doppler) in order to provide the required depth of an accurate ultrasonic probing of a preset area. An ultrasonic Doppler transducer is placed on the patient's closed eyelids and an ultrasonic beam is directed onto the projection of the short ciliary arteries to obtain a clear-cut "arterial tone" ultrasonic signal, thus taking notice of the maximum values of the linear and volumetric blood flow velocity in the ciliary arteries. Thus, should the linear blood flow velocity be equal to 9 cm/s and the volumetric blood flow to 5 ml/min the optic nerve blood supply is normal, and if the value of said velocities is below that specified above, one should proceed with treatment of optic nerve blood supply insufficiency.

The proposed method can be carried into effect with the aid of any heretofore-known ultrasonic apparatus of the aforestated application.

The proposed method has passed clinical trials on 350 patients (700 eyes) with optic nerve atrophy or suspected of that disease as well as on persons free from any eye diseases. This has made it possible to find out the state parameters of optic nerve blood supply in norm, at the initial stages of optic nerve blood supply disturbance, wherein no clinical manifestations are yet observed, and at a stage of already advanced disease, and to effect treatment aimed at improving the state of optic nerve blood supply.

To promote understanding of the present invention given below are the following examples of clinical application of the method disclosed herein.

EXAMPLE 1

Male patient I., 22. Diagnosis: suspicion for partial atrophy of the right-eye optic nerve. Left eye unaffected.

The patient was examined in a sitting posture with the eyes closed. A sagittal eye tomogram was obtained by virtue of ultrasonic scanning at the level of the optic nerve, whereupon the thus-obtained tomogram was presented on a display. Then a distance from the eyelid anterior surface to the projection of the ciliary arteries supplying the optic nerve, was measured on the presented eye scanogram. The data obtained (a distance of 22.5 mm) were entered into a pulsating-wave ultrasonic Doppler instrument (pulse-Doppler) so as to provide the required depth of an accurate ultrasonic probing of a preset area. An ultrasonic Doppler transducer was put onto the patient's closed eyelids and an ultrasonic beam was directed onto the projection of the short ciliary arteries to obtain a clear-cut "arterial tone" ultrasonic signal, thus taking down the maximum values of the linear blood flow velocity and the volumetric blood flow velocity in the ciliary arteries. Found: linear blood flow velocity in the right eye, 6 cm/s, volumetric blood flow, 3 ml/min; linear blood flow velocity in the left eye, 9.5 cm/s, volumetric blood flow, 5 ml/s.

Conclusion: the linear blood flow velocity equal to 6 cm/s and the volumetric blood flow equal to 3 ml/min give evidence of an insufficient blood supply in the right eye, which involves a necessary treatment, whereas the linear blood flow velocity equal to 9.5 cm/s and the volumetric blood flow equal to 5 ml/min are indicative of the normal blood supply of the left eye.

EXAMPLE 2

Male patient U., 22. Diagnosis: both eyes in a sound state, ocular fundus in norm, visual acuity 1.0, no complaints.

The patient was examined in a sitting posture with the eyes closed. A sagittal eye tomogram was obtained by virtue of ultrasonic scanning at the level of the optic nerve, whereupon the thus-obtained tomogram was presented on a display. Then a distance from the eyelid anterior surface to the projection of the ciliary arteries supplying the optic nerve, was measured on the presented eye scanogram. The date thus obtained (a distance of 21.5 mm) were entered into a pulsating-wave ultrasonic Doppler instrument (pulse-Doppler) so as to provide the required depth of an accurate ultrasonic probing of a preset area. An ultrasonic Doppler transducer was put onto the patient's closed eyelids and an ultrasonic beam was directed onto the projection of the short ciliary arteries to obtain a clear-cut "arterial tone" ultrasonic signal, thus registering the maximum values of the linear blood flow velocity and the volumetric blood flow velocity in the ciliary arteries. The data found on the part of both OD and OS were similar and equalled as follows: linear blood flow velocity, 12.5 cm/s, volumetric blood flow, 6 ml/min.

Conclusion: the linear blood flow, velocity equal to 12.5 cm/s and the volumetric blood flow equal to 6 ml/min are indicative of a normal blood supply of the optic nerve in both eyes. No treatment is required.

EXAMPLE 3

Male patient B., 45. Diagnosis: atrophy of the optic nerves in both eyes. The patient was examined in a sitting posture with the eyes closed. A sagittal eye tomogram was obtained by virtue of ultrasonic scanning at the level of the optic nerve, whereupon the thus-obtained tomogram was presented on a display. Then a distance from the eyelid anterior surface to the projection of the ciliary arteries supplying the optic nerve, was measured on the eye scanogram displayed. The data obtained (a distance of 20.5 mm) were entered into a pulsating-wave ultrasonic Doppler instrument (pulse-Doppler) so as to provide the required depth of an accurate ultrasonic probing of a preset area. An ultrasonic Doppler transducer was put onto the patient's closed eyelids and an ultrasonic beam was directed onto the projection of the short ciliary arteries to obtain a clear-cut "arterial tone" ultrasonic signal, thus registering the maximum values of the linear blood flow velocity and the volumetric blood flow velocity in the ciliary arteries. The data found were as follows: linear blood flow velocity—OS, 4.5 cm/s; OD, 3 cm/s; volumetric blood flow—OS, 1 ml/min; OD, 0.5 ml/min.

Conclusion: the linear blood flow velocity of 4.5 cm/s in the left eye and of 3 cm/s in the right eye, as well as the volumetric blood flow of 1 ml/min in the left eye and of 0.5 ml/min in the right eye are indicative of an inadequate blood flow in the ciliary arteries of both eyes and hence point to a poor blood supply of the optic nerves and give grounds for an appropriate a treatment.

EXAMPLE 4

Male patient M., 64. Diagnosis: atrophy of the optic nerves in both eyes.

The patient was examined in a sitting posture with the eyes closed. A sagittal eye tomogram was obtained by virtue of ultrasonic scanning at the level of the optic nerve, whereupon the thus-obtained tomogram was presented on a display. Then a distance from the eyelid anterior surface to the projection of the ciliary arteries supplying the optic nerve, was measured on the eye scanogram displayed. The data obtained were entered into a pulsating-wave ultrasonic Doppler instrument (pulse-Doppler) so as to provide the required depth of an accurate ultrasonic probing of a preset area. An ultrasonic Doppler transducer was put onto the patient's closed eyelids and an ultrasonic beam was directed onto the projection of the short ciliary arteries to obtain a clear-cut "arterial tone" ultrasonic signal, thus registering the maximum values of the linear blood flow velocity and the volumetric blood flow velocity in the ciliary arteries. Found: linear blood flow velocity—OD, 2 cm/s; OS, 5 cm/s; volumetric blood flow—OD, 0 ml/min; OS, 2 ml/min.

Conclusion: the linear blood flow velocity of 2 cm/s in the right eye and of 5 cm/s in the left eye, as well as the volumetric blood flow of 0 ml/min in the right eye and of 2 ml/min in the left eye are indicative of an inadequate blood supply of the optic nerve in both eyes and point to the fact that an appropriate treatment should be resorted to.

EXAMPLE 5

Male patient F., 24. Diagnosis: suspicion for partial atrophy of the right-eye optic nerve. Left eye unaffected.

The patient was examined in a sitting posture with the eyes closed. A sagittal eye tomogram was obtained by virtue of ultrasonic scanning at the level of the optic nerve, whereupon the thus-obtained tomogram was presented on a display. Then a distance from the eyelid anterior surface to the projection of the ciliary arteries supplying the optic nerve, was measured on the eye scanogram displayed. The data obtained (a distance of 21 mm) were entered into a pulsating-wave ultrasonic Doppler instrument (pulse-Doppler) so as to provide the required depth of an accurate ultrasonic probing of a preset area. An ultrasonic Doppler transducer was put onto the patient's closed eyelids and an ultrasonic beam was directed onto the projection of the ciliary arteries to obtain a clear-cut "arterial tone" ultrasonic signal, thus registering the maximum values of the linear blood flow velocity and the volumetric blood flow velocity in the ciliary arteries. Found: linear blood flow velocity—OD, 3 cm/s; OS, 5 cm/s; volumetric blood flow—OD, 0.5 ml/min; OS, 1 ml/min.

Conclusion: the linear blood flow velocity of 3 cm/s and the volumetric blood flow of 0.5 ml/min in the right eye are indicative of an inadequate blood supply of the right-eye optic nerve, and the linear blood flow velocity of 5 cm/s and the volumetric blood flow of 1 ml/min in the left eye give evidence of an insufficient blood supply of the left eye (further more comprehensive examinations detected deviations from norm in the visual function). An appropriate treatment is needed.

EXAMPLE 6

Male patient I., 29. Diagnosis: initial atrophy of the left-eye optic nerve. Suspicion for subatrophy of the right-eye optic nerve.

The patient was examined in a sitting posture with the eyes closed. A sagittal eye tomogram was obtained by virtue of ultrasonic scanning at the level of the optic nerve, whereupon the thus-obtained tomogram was presented on a display. Then a distance from the eyelid anterior surface to the projection of the ciliary arteries supplying the optic nerve, was measured on the eye scanogram displayed. The data obtained (a distance of 22.5 mm) were entered into a pulsating-wave ultrasonic Doppler instrument (pulse-Doppler) so as to provide the required depth of an accurate ultrasonic probing of a preset area. An ultrasonic Doppler transducer was put onto the patient's closed eyelids and an ultrasonic beam was directed onto the projection of the ciliary arteries to obtain a clear-cut "arterial tone" ultrasonic signal, thus registering the maximum values of the linear blood flow velocity and the volumetric blood flow in the ciliary arteries. Found: linear blood flow velocity—OS, 4 cm/s; OD, 5.5 cm/s; volumetric blood flow velocity—OS, 0.5 ml/min; OD, 3 ml/min.

Conclusion: the linear blood flow velocity of 5.5 cm/s and the volumetric blood flow of 3 ml/min in the right eye point to an insufficient blood supply of the right-eye optic nerve, while the linear blood flow velocity of 4 cm/s and the volumetric blood flow of 0.5 ml/min testify to an insufficient blood supply of the left-eye optic nerve, which evidences that an appropriate treatment is required.

EXAMPLE 7

Male patient R., 21. Diagnosis: suspicion for atrophy of the right-eye optic nerve. Subatrophy of the left-eye optic nerve.

The patient was examined in a sitting posture with the eyes closed. A sagittal eye tomogram was obtained by virtue of ultrasonic scanning at the level of the optic nerve, whereupon the thus-obtained tomogram was presented on a display. Then a distance from the eyelid anterior surface to the projection of the ciliary arteries supplying the optic nerve, was measured on the eye scanogram displayed. The data obtained (a distance of 24.5 mm) were entered into a pulsating-wave ultrasonic Doppler instrument (pulse-Doppler) so as to provide the required depth of an accurate ultrasonic probing of a preset area. An ultrasonic Doppler transducer was put onto the patient's closed eyelids and an ultrasonic beam was directed onto the projection of the ciliary arteries supplying the optic nerve, so as to obtain a clearcut "arterial tone" ultrasonic signal, thus registering the maximum values of the linear blood flow velocity and the volumetric blood flow velocity in the ciliary arteries. Found: linear blood flow velocity—OD, 6 cm/s; OS, 4 cm/s; volumetric blood flow —OD, 3 ml/min; OS, 2 ml/min.

Conclusion: the linear blood flow velocity of 6 cm/s and the volumetric blood flow of 3 ml/min point to an insufficient blood supply of the right-eye optic nerve, while the linear blood flow velocity of 4 cm/s and the volumetric blood flow of 2 ml/min are indicative of an insufficient blood supply of the left-eye optic nerve, which in turn evidences that an appropriate treatment is needed.

EXAMPLE 8

Male patient Sh., 43. Diagnosis: suspicion for atrophy of the optic nerve in both eyes.

The patient was examined in a sitting posture with the eyes closed. A sagittal eye tomogram was obtained by virtue of ultrasonic scanning at the level of the optic nerve, whereupon the thus-obtained tomogram was presented on a display. Then a distance from the eyelid anterior surface to the projection of the ciliary arteries supplying the optic nerve, was measured on the eye scanogram displayed. The data obtained (a distance of 23.5 mm) were entered into a pulsating-wave ultrasonic Doppler instrument (pulse-Doppler) so as to provide the required depth of an accurate ultrasonic probing of a preset area. An ultrasonic Doppler transducer was put onto the patient's closed eyelids and an ultrasonic beam was directed onto the projection of the ciliary arteries to obtain a clear-cut "arterial tone" ultrasonic signal, thus registering the maximum values of the linear blood and flow velocity and the volumetric blood flow velocity in the ciliary arteries. Found: linear blood flow velocity—OD, 4.5 cm/s; OS, 5 cm/s; volumetric blood flow —OD, 2 ml/min; OS, 2 ml/min.

Conclusion: the linear blood flow velocity of 4.5 cm/s and the volumetric blood flow of 2 ml/min point to an insufficient blood supply of the right-eye optic nerve, while the linear blood flow of 5 cm/s and the volumetric blood flow of 2 ml/min are indicative of an insufficient blood supply of the left-eye optic nerve, which in turn evidences that an appropriate treatment is needed.

What we claim is:

1. A method for diagnosing an early stage of optic nerve blood supply disturbance which comprises determining the state and localization of the optic nerve by ultrasonic scanning, measuring the distance from the eyelid anterior surface to the ciliary arteries supplying said optic nerve, and determining the state of hemodynamics in said ciliary arteries using the measured distance with the aid of ultrasonic pulse-dopplerography, by measuring the linear blood flow velocity and the volumetric blood flow velocities in said arteries, wherein the value of said linear blood flow velocity 4 below 9 cm/s and that of said volumetric blood flow 4 below 5 ml/min are indicative of an early stage of optic nerve blood supply disturbance.

* * * * *